United States Patent [19]
Kalopissis et al.

[11] 4,042,627
[45] Aug. 16, 1977

[54] DIPHENYLAMINES FOR DYEING KERATINOUS FIBERS

[75] Inventors: Grégoire Kalopissis, Paris; Andreé Bugaut, Boulogne-sur-Seine; Françoise Estradier, Paris, all of France

[73] Assignee: L'Oreal, Paris, France

[21] Appl. No.: 618,244

[22] Filed: Sept. 30, 1975

Related U.S. Application Data

[60] Continuation of Ser. No. 396,296, Sept. 11, 1973, abandoned, which is a division of Ser. No. 270,650, July 11, 1972, Pat. No. 3,787,174, which is a continuation-in-part of Ser. No. 61,833, Aug. 6, 1970, Pat. No. 3,792,090.

[30] Foreign Application Priority Data

July 14, 1971   Luxembourg ............................ 63527
Aug. 11, 1969   Luxembourg ............................ 59265

[51] Int. Cl.² .......................................... C07C 91/42
[52] U.S. Cl. ...................... 260/571; 8/10.2; 8/11; 260/396 N; 260/553 A; 260/562 A; 260/562 P; 260/573; 260/42.21; 424/71
[58] Field of Search ............... 260/571, 562 A, 562 P, 260/571

[56] References Cited

U.S. PATENT DOCUMENTS 3,443,943   5/1969   Rogers ..................................... 96/29
3,471,576   10/1969   Klesper et al. ......................... 260/571

*Primary Examiner*—Arthur P. Demers
*Attorney, Agent, or Firm*—Cushman, Darby & Cushman

[57] ABSTRACT

Diphenylamines of the formula

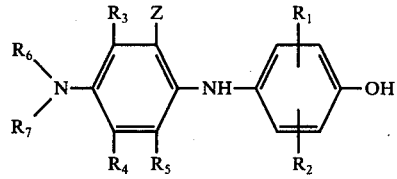

wherein $R_1$ and $R_2$ each independently represent hydrogen, halogen or lower alkyl containing 1-4 carbon atoms with at least one of $R_1$ and $R_2$ being other than hydrogen; $R_3$, $R_4$, $R_5$, $R_6$, and $R_7$ each independently represent hydrogen or lower alkyl optionally substituted with hydroxy, carbamyl, piperidinyl or acylamino; $R_3$ and $R_6$ or $R_4$ and $R_7$ also optionally forming together with the carbon and nitrogen atoms to which they are attached, a dihydrooxazine or pyrroline heterocycle; and Z represents amino, acylamino or hydroxy; and the acid salts of said diphenylamines. These diphenylamines are usefully employed in cosmetic compositions for the hair including hair dye compositions and hair setting lotion compositions.

3 Claims, No Drawings

DIPHENYLAMINES FOR DYEING KERATINOUS FIBERS

This application is a continuation of application Ser. No. 396,296, filed Sept. 11, 1973, now abandoned, which is a division of application Ser. No. 270,650, filed July 11, 1972, now U.S. Pat. No. 3,787,174 which is a continuation-in-part of Ser. No. 61,833, filed Aug. 6, 1970, now U.S. Pat. No. 3,792,090.

This invention relates to novel leuco derivatives of indoanilines, a process for preparing the same and to novel cosmetic compositions containing these leuco derivatives for dyeing keratinic fibers such as human hair. The leuco derivatives of indoanilines of this invention are colorless compounds which when applied in an aqueous solution to the fibers to be dyed, oxidize in the air or in the presence of another oxidizing agent thereby giving the corresponding indoanilines, which on the other hand are colored compounds directly responsible for dyeingof the fiber. The dyes thus obtained present qualities of fastness and intensity of dyeing superior to those dyeings obtained by direct application of indoanilines, because of the better solubility of the leucoderivatives of these compounds.

More specifically, the present invention relates to a compound of the formula:

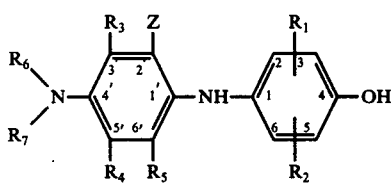

(I)

wherein $R_1$ and $R_2$ each independently represent a member selected from the group consisting of hydrogen, halogen, and lower alkyl containing 1–4 carbon atoms, with the proviso that at least one of $R_1$ and $R_2$ is other than hydrogen; $R_3$, $R_4$ and $R_5$ each independently are selected from the group consisting of hydrogen, lower alkyl containing 1–4 carbon atoms and lower alkyl containing 1–4 carbon atoms and substituted with a member selected from the group consisting of hydroxy, carbamyl, piperidinyl and acylamino; $R_6$ is selected from the group consisting of hydrogen, lower alkyl containing 1–4 carbon atoms, lower alkyl containing 1–4 carbon atoms and substituted with a member selected from the group consisting of hydroxy, carbamyl, piperidinyl and acylamino, and together with $R_3$ and the nitrogen atom to which $R_6$ is attached form a heterocycle selected from the group consisting of dihydrooxazine and pyrroline; $R_7$ is selected from the group consisting of hydrogen, lower alkyl containing 1–4 carbon atoms, lower alkyl containing 1–4 carbon atoms and substituted with a member selected from the group consisting of hydroxy, carbamyl, piperidinyl and acylamino, and together with $R_4$ and the nitrogen atom to which $R_7$ is attached form a heterocycle selected from the group consisting of dihydro-oxazine and pyrroline; Z represents a member selected from the group consisting of amine, acylamino and hydroxy and the salts formed by these compounds with organic or inorganic acids, in particular, their oxalates, hydrochlorides or tartrates.

The novel diphenylamines according to the invention can be obtained by two different processes.

The first process comprises reducing the corresponding indoanilines of the formula

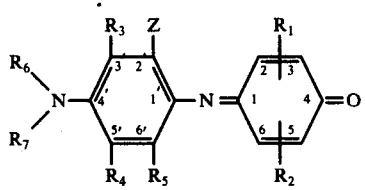

wherein $R_1$ to $R_7$ and Z have the meaning indicated above, said reduction being performed either in an aqueous alkaline medium with a reducing agent such as sodium hydrosulfite or ammonium sulfide, or in a solvent such as an alcohol, for instance, ethanol, by catalytic hydrogenation at ambient pressure in the presence, for example, of palladium on barium sulfate or on carbon.

When the process is carried out in an aqueous alkaline medium, the pH of said medium ranges generally between about 9–12, said pH having been attained generally by the inclusion therein of an alkalizing agent such as sodium hydroxide or the like. The amount of reducing agent employed can vary but generally it will be present in amounts such that the mole ratio of indoaniline being reduced to reducing agent ranges between 1:1.5 to 1:3. This reducing reaction is generally carried out at ambient pressure and at a temperature ranging from about 25° to 50° C.

Alternatively, the reduction of the above indoaniline can be carried out in a solvent selected from the group consisting of ethanol and ethylacetate by catalytic hydrogenation at ordinary pressure and a temperature of 20° to 50° in the presence of catalytic amounts of palladium on a substrate selected from the group consisting of barium sulfate and carbon. Generally, the amount of the catalyst, i.e., the palladium on said substrate, ranges between about 10 to 25 percent by weight of the indoaniline being reduced.

The second process, which makes it possible to obtain the diphenylamines of formula (I) wherein radicals $R_6$ and $R_7$ both designate a hydrogen atom, and Z is $NH_2$, comprises condensing a dinitro derivative of the formula:

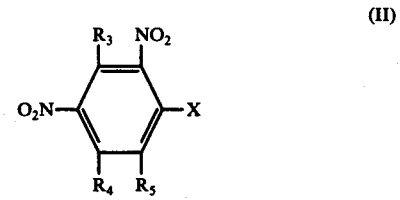

(II)

wherein $R_3$, $R_4$ and $R_5$ have the meaning given above and X represents a halogen atom, on a substituted paraaminophenol of the formula:

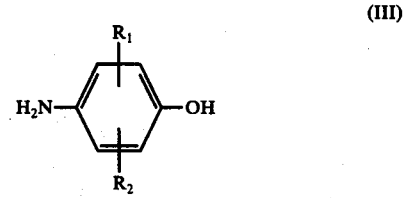

(III)

wherein $R_1$ and $R_2$ have the meaning given above, thereby obtaining a dinitrodiphenylamine of the formula:

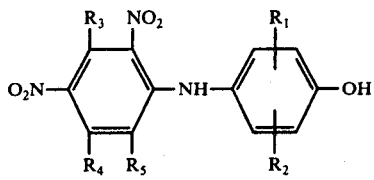

which is then reduced by sodium hydrosulfite in an alkaline medium or by catalytic hydrogenation in a suitable solvent, such as an alcohol, for instance, ethanol. In this second process the molar ratio of said dinitro derivative to said substituted paraaminophenol is generally 1 : 1 , and the condensation reaction is ordinarily carried out at the reflux temperature of the solvent employed at ordinary pressure.

The reduction of the resulting dinitrodiphenylamine can, as stated above, be carried out in an aqueous alkaline medium having a pH ranging from about 9 to 12, the pH having been attained generally by the inclusion therein of an alkalizing agent such as sodium hydroxide or the like. The amount of reducing agent employed can vary. This reducing reaction is generally carried out at ambient pressure and at a temperature ranging from about 30° to 60° C.

Alternatively, the reduction of the above dinitrodiphenylamine can be carried out in a solvent such as ethanol by catalytic hydrogenation at ordinary pressure and a temperature of 20° to 50° in the presence of catalytic amounts of palladium on a substrate selected from the group consisting of barium sulfate and carbon. Generally the amount of the catalyst, i.e., the palladium on said substrate, ranges between about 10 to 25 percent by weight of the dinitrodiphenylamine being reduced.

The diphenylamines of the present invention are usefully employed to dye keratinous fibers, particularly human hair. When applied to human hair, these compounds, in an aqueous or dilute alcohol solution having a pH ranging from 4 to 11, and in extremely slight concentrations because of their good affinity for keratinous fibers and the power of the dyes obtained after oxidation either in the air or by another oxidizing agent such as hydrogen peroxide, provide an extremely rich range of shades ranging from very luminous violets to ash or silver grays passing through blues, greens, reds, pinks and golden, copper or ash blonds. The dyeings thus obtained are always characterized by their richness in glints and the pearly appearance they impart to the hair.

Thus, the present invention also relates to a dyeing composition for keratinous fibers, particularly human hair, comprising an aqueous or dilute alcohol solution of at least one compound of formula (I) or a salt of such a compound.

The dyeing compositions according to the invention can contain only the compounds of formula (I). However, they can also contain other known leuco derivatives of indoanilines, indamines or indophenols, or again oxidation dyes, such as o- or p-phenylenediamines or o- or p-aminophenols or again direct dyes.

The concentration of the compounds of formula (I) in the dyeing composition according to the present invention can vary between 0.002 and 2% and generally between 0.005 and 0.5% by weight.

The pH of the dye compositions according to the present invention can vary between 4 and 11. To regulate this pH at the desired value, there can be used as the alkalizing agent, ammonia, mono-, di- or triethanolamine, and as an acidifying agent phosphoric acid, acetic acid or lactic acid.

The dye composition according to the present invention is generally in the form of an aqueous solution, to which most often a low molecular weight alcohol, such an ethanol or isopropanol, has been added in a proportion of 20 to 70% by weight. Rather than a low molecular weight alcohol a glycol, such as propyleneglycol or butylglycol, can be employed in amounts of about 1 to 6% by weight. The alcohol or the glycol facilitate putting the diphenylamines into solution.

Dyeing of keratinous fibers, and particularly human hair, with the dye compositions of the present invention is performed in the usual way by applying said composition to the fibers to be dyed, said composition being left in contact with the fibers for a time varying from 10 to 30 minutes. Following this application the fibers can be rinsed and if desired, washed. Thereafter, the thus treated fibers are dried. If a simultaneous bleaching of the fiber is desired, there can be added to the composition, before its application, either hydrogen peroxide in amounts of 20 to 60% in weight, or hydrogen peroxide of 20 volumes, that is to say 4 to 12% in weight of $H_2O_2$, or an equivalent quantity of another oxidizing agent of said composition.

In another embodiment of the present invention, the novel diphenylamines can also be employed in the production of capillary hair-setting lotions. These lotions comprise an aqueous alcohol solution, at least one diphenylamine of Formula I or a salt thereof and at least one cosmetic resin. The amount of diphenylamine or its salt, as defined above, present in the hair-setting lotion according to this invention can be extremely slight. Such an amount generally varies between 0.002 and 1% by weight and preferably between 0.002 and 0.5% by weight of the total hair-setting lotion composition, the pH of which generally lies between 5-8.

Representative cosmetic resins that can be employed in the hair-setting lotions of the present invention include, for instance, polyvinyl pyrrolidone having a molecular weight of 40,000–400,000, copolymer of crotonic acid and vinyl acetate, said copolymer having a molecular weight ranging from about 10,000 to 70,000 copolymer of vinyl pyrrolidone and vinyl acetate wherein the ratio of VP to VA ranges between 50–70:5-0–30, said copolymer having a molecular weight ranging from about 30,000 to 200,000 and maleic anhydride-butylvinyl ether copolymer, a 1% solution of which in methylethyl ketone has a viscosity of 0.1–3.5 cps at 25° C. These resins are used in a proportion of about 1 to 3 percent by weight of the hair-setting lotion composition.

The alcohols suitable for the preparation of the hair-setting lotions according to the invention are low molecular weight alkanols, such as ethanol or isopropanol, which are present in amounts of about 20 to 70% by weight of the hair-setting lotion composition.

The hair-setting lotions of the present invention impart to the hair a great variety of shades located in the ash blond, golden blond, ash gray or silver gray tones and which tones can even be shaded violet, mauve, blue or pink. The colorings obtained are characterized by a pearly appearance and a great richness of glints and by their regularity or evenness even in the case of application to irregularly bleached hair.

The hair-setting lotions according to the invention are usually employed by application to wet hair, previously washed and rinsed, followed by rolling the hair up on curlers and drying the hair.

The following examples are intended to illustrate the present invention. Unless otherwise specified all parts and percentages are by weight and all temperatures are expressed in degrees centigrade.

EXAMPLE 1

4-hydroxy 3,5'-dimethyl 2', 4'-diamino diphenylamine is prepared according to the following reaction:

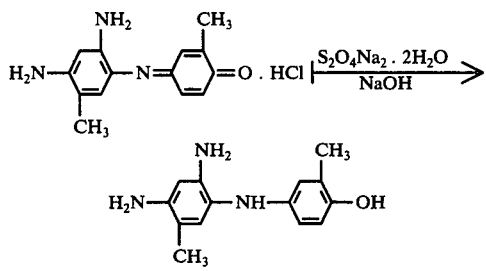

0.0086 mole (2.41 g) of sodium hydrosulfite of 75% purity, is dissolved in 27.5 cc of a 0.5 N soda solution. To this solution, 0.00342 mole (0.950 g) of N-[(2', 4'-diamino 5'-methyl) phenyl] 3-methyl benzoquinone imine hydrochloride in suspension in 5 cc of 95° ethanol is added gradually, with stirring, keeping the temperature in the vicinity of 30° C. When the addition has been completed, the reaction mixture is allowed to become totally colorless. Then acetic acid is added to this reaction mixture until neutrality is reached, thereby precipitating the above diphenylamine which is then filtered under nitrogen, washed with water and dried under vacuum for 5 hours at 80° C. 0.60 g of pure product, which melts at 229° C, is thus obtained. Molecular weight calculated for $C_{14}H_{17}N_3O$ = 243 Molecular weight found by potentiometric determination in acetic acid by perchloric acid = 245

| Analysis | Calculated for $C_{14}H_{17}N_3O$ | Found | |
|---|---|---|---|
| C % | 69.11 | 69.38 | 69.01 |
| H % | 7.04 | 6.92 | 7.04 |
| N % | 17.27 | 17.24 | 17.36 |

EXAMPLE 2

4-hydroxy 3-chloro 2', 4'-diamino diphenylamine and its dihydrochloride, monohydrate are prepared as follows:

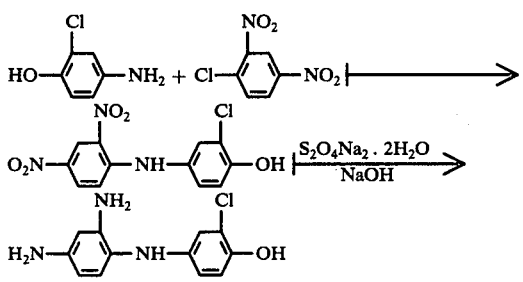

1st phase — Preparation of 4-hydroxy 3-chloro 2', 4'-dinitro diphenylamine

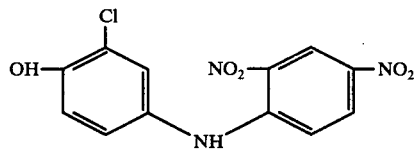

Into 65 cc of absolute ethanol there are introduced, on the one hand, 0.025 mole (4.5 g) of 2-chloro 4-amino phenol hydrochloride, and, on the other hand, 0.025 mole (5.06 g) of 2,4-dinitro chlorobenzene and 6.2 g of molten sodium acetate. The mixture is brought to reflux, with stirring, for 6 hours then filtered while boiling to eliminate the inorganic salts.

50 cc of water are then added to the alcohol filtrate which is then cooled to 0° C. 4-hydroxy-2-methyl 2', 4'-dinitro diphenylamine, which precipitates, is filtered therefrom and this product, after washing in water, recrystallization in an ethanol-water mixture and drying under vacuum, melts at 189°.

| Analysis | Calculated for $C_{12}H_8N_3O_5Cl$ | Found | |
|---|---|---|---|
| C % | 46.52 | 46.48 | 46.67 |
| H % | 2.58 | 2.48 | 2.62 |
| N % | 13.51 | 13.47 | 13.58 |
| Cl | 11.47 | 11.56 | 11.52 |

2nd phase — Preparation of 4-hydroxy 3-chloro 2', 4'-diamino diphenylamine 0.07 mole (20 g) of sodium hydrosulfite of 75% purity is dissolved in 120 cc of normal soda solution. To this solution there is added gradually, with good stirring, while keeping the temperature in the vicinity of 35° C, 0.009 mole (2.79 g) of the dinitro derivative previously obtained in the first phase above. When the addition is completed and the reaction mixture colorless, it is neutralized with acetic acid thereby precipitating the above diphenylamine.

After filtering this diphenylamine from the reaction mass, washing with water and drying it under vacuum, the product melts at 203°.

| Analysis | Calculated for $C_{12}H_{12}N_3OCl$ | Found | |
|---|---|---|---|
| C % | 57.74 | 57.58 | 57.75 |
| H % | 4.84 | 4.87 | 4.87 |
| N % | 16.83 | 16.70 | 16.97 |

1 g of this diphenylamine thus obtained is then dissolved in 5 cc of a 2 N hydrochloric solution. The resulting solution is cooled to −10°. Then 15 cc of hydrochloric acid at 22° B are added. The 4-hydroxy 3-chloro 2', 4'-diamino diphenylamine dihydrochloride, monohydrate crystallizes. After filtering and drying under vacuum for 3 hours, it melts with decomposition at 225°.

Molecular weight calculated for $C_{12}H_{12}N_3OCl \cdot 2HCl, H_2O$ = 340.5

Molecular weight found by potentiometric determination in water with 0.1 N soda solution = 343

EXAMPLE 3

4-hydroxy 2-methyl 2', 4'-diamino diphenylamine is prepared in accordance with the following reaction:

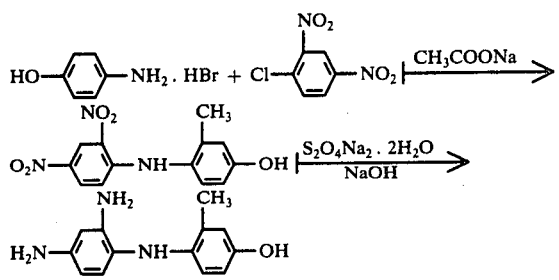

1st phase — Preparation of 4-hydroxy 2-methyl 2′, 4′-dinitro diphenylamine.

Into 65 cc of absolute ethanol there are introduced, on the one hand, 0.025 mole (5.1 g) of 3-methyl 4-amino phenol hydrobromide, and, on the other hand, 0.025 mole (5.06 g) of 2,4-dinitro chlorobenzene and 6.2 g molten sodium acetate. The resulting mixture is brought to reflux and kept there with stirring for four hours, after which it is filtered while boiling to eliminate inorganic salts. 50 cc of water are then added to the alcohol filtrate which is then cooled to 0° C. 4-hydroxy 2-methyl 2′, 4′-dinitro diphenylamine, which has precipitated, is then filtered therefrom. This product, after washing with water, recrystallization in an ethanol-water mixture and drying under vacuum, melts at 165°.

| Analysis | Calculated for $C_{13}H_{11}N_3O_5$ | Found | |
|---|---|---|---|
| C % | 53.98 | 54.14 | 53.91 |
| H % | 3.83 | 3.87 | 3.90 |
| N % | 14.53 | 14.49 | 14.39 |

2nd phase — Preparation of 4-hydroxy 2-methyl 2′, 4′-diamino diphenylamine.

0.071 mole (20 g) of sodium hydrosulfite of 75% purity is dissolved in 140 cc of normal soda solution. 0.0103 mole (3 g) of the dinitro derivative obtained in the 1st phase is then gradually added to this solution with good stirring, while keeping the temperature in the vicinity of 35° C. When the addition is completed and the reaction mixture is colorless, it is neutralized with acetic acid thereby precipitating the above diphenylamine which is then filtered, washed with water and dried under vacuum five fours at 80°. 1.94 g of this pure product, which melts at 163° are thus obtained.

| Analysis | Calculated for $C_{13}H_{15}N_3O$ | Found | |
|---|---|---|---|
| C % | 68.10 | 68.02 | 67.91 |
| H % | 6.59 | 6.62 | 6.64 |
| N % | 18.33 | 18.22 | 18.33 |

EXAMPLE 4

4-hydroxy 3-methyl 5′-methoxy 2′,4′-diamino diphenylamine is prepared in accordance with the following reaction:

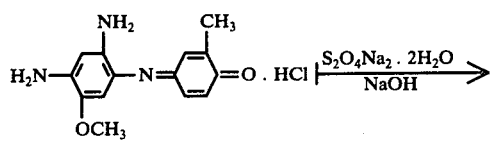

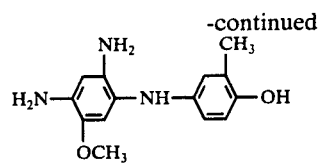

To 160 cc of a 1.25 N soda solution containing in solution 0.05 mole (14 g) of sodium hydrosulfite of 75% purity there is added gradually, with good stirring and keeping the reaction mixture in the vicinity of 30° C, 0.02 mole (5.87 g) of N-[(2′,4′-diamino 5′-methoxy) phenyl] 3-methyl benzoquinone imine hydrochloride in suspension in 30 cc of ethanol at 95°. When the addition is finished and the reaction mixture is completely colorless, rapid filtering under nitrogen is performed, followed by neutralizing with acetic acid to precipitate the above diphenylamine. This diphenylamine product is isolated by filtering, after which it is washed with water and then dried 5 hours under vacuum at 80°. 4.3 g of chromatographically pure product, which melts at 204° are then obtained.

Molecular weight calculated for $C_{14}H_{17}N_3O_2$ = 259
Molecular weight found by potentiometric determination in acetic acid by perchloric acid = 260

| Analysis | Calculated for $C_{14}H_{17}N_3O_2$ | Found | |
|---|---|---|---|
| C % | 64.84 | 65.09 | 65.12 |
| H % | 6.61 | 6.71 | 6.74 |
| N % | 16.21 | 15.98 | 16.12 |

EXAMPLE 5

4-hydroxy 2-chloro 2′,4′ -diamino diphenylamine is prepared in accordance with the following reaction:

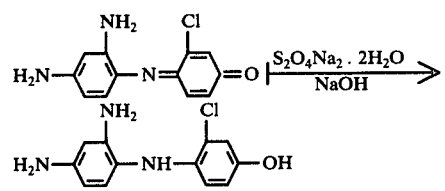

To 160 cc of a 1.25 N soda solution in which has been dissolved 0.05 mole (14g) of sodium hydrosulfite of 75% purity there is added gradually, with good stirring, 0.02 mole (5.95 g) of N-[(2′,4′-diamino) phenyl] 2-chloro benzoquinone imine in suspension in 40 cc of ethanol at 95°. When the addition is finished, the reaction mixture is kept at 35° C until total loss of color. Thereafter the reaction mixture is cooled and neutralized with acetic acid, thereby precipitating the above diphenylamine. After washing this diphenylamine with water and drying it under vacuum 5 hours at 80° C, 5.42 g of the pure product, which melts at 173°, are obtained.

Molecular weight calculated for $C_{12}H_{12}N_3OCl$ = 249.5
Molecular weight found by potentiometric determination in acetic acid by perchloric acid = 252

| Analysis | Calculated for $C_{12}H_{12}N_3OCl$ | Found | |
|---|---|---|---|
| C % | 57.74 | 57.85 | 57.78 |
| H % | 4.84 | 4.95 | 4.86 |
| N % | 16.83 | 16.58 | 16.72 |

EXAMPLE 6

4-hydroxy 2,6,3',5'-tetramethyl 2',4'-diamino diphenylamine is prepared in accordance with the following reaction:

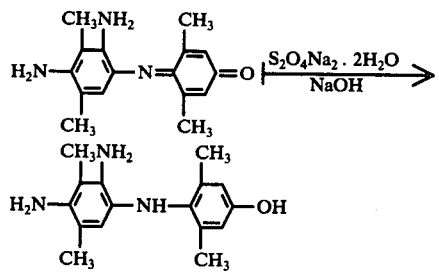

0.05 mole (14 g) of sodium hydrosulfite of 75% purity is dissolved in 150 cc of 1.25 N soda. To this solution there is added gradually, with good stirring, keeping the temperature in the vicinity of 40° C, 0.02 mole (5.38 g) of N-[(2',4'-diamino 3',5'-dimethyl) phenyl] 2,6-dimethyl benzoquinone imine in suspension in 40 cc of ethanol at 95°. The reduction reaction is rather slow. However, when the reaction mixture is colorless, it is neutralized with acetic acid thereby precipitating the above diphenylamine which is then filtered, washed with water and dried under vacuum for 5 hours at 80°. 5.01 g of this pure diphenylamine, which melts at 250°, are thus obtained.

Molecular weight calculated for $C_{16}H_{21}N_3O$ = 271
Molecular weight found by potentiometric determination in acetic acid by perchloric acid = 273

| Analysis | Calculated $C_{16}H_{21}N_3O$ | Found | |
|---|---|---|---|
| C % | 70.82 | 70.43 | 70.55 |
| H % | 7.80 | 7.43 | 7.81 |
| N % | 15.49 | 15.53 | 15.51 |

EXAMPLE 7

Second method of preparing the 4-hydroxy 2,6,3',5'-tetramethyl 2',4'-diamino diphenylamine described in Example 6:

0.027 mole (0.74 g) of N-[(2',4'-diamino 3',5'-dimethyl) phenyl] 2,6-dimethyl benzoquinoneimine is dissolved in 45 L cc of water and 30 cc of ethyl alcohol. To this resulting solution there are added gradually at 25°, with stirring, 3.5 cc of an ammonia solution at 16° Be previously saturated with sulfurated hydrogen. The completely colorless reaction mixture is then cooled at 0°, thereby precipitating the above diphenylamine which is then filtered and washed with water. There is thus obtained, after drying the said diphenylamine under vacuum at 80°, 0.65 g of the pure product which melts at 250° and which is identical with the product prepared in Example 6.

EXAMPLE 8

4-hydroxy 3,5,3',5'-tetramethyl 2',4'-diamino diphenylamine and its dihydrochloride are prepared as follows:

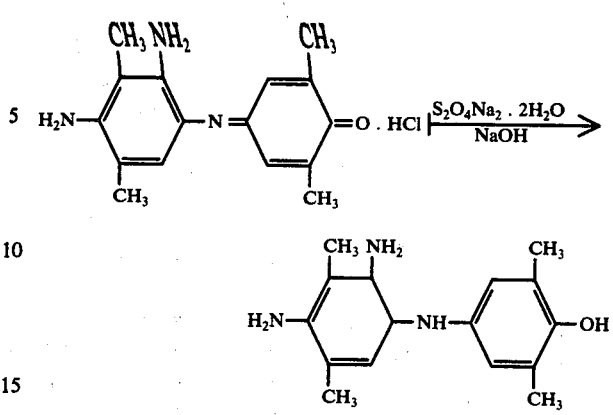

0.01 mole (3.05 g) of N-[(2',4'-diamino 3',5'-dimethyl) phenyl] 3,5-dimethyl benzoquinoneimine hydrochloride is dissolved in 90 cc of water and 60 cc of 95° ethanol. To this dilute alcohol solution there are added, drop by drop, with stirring and at 25°, 9 cc of an aqueous ammonia solution at 16° Be previously saturated with sulfurated hydrogen. The reaction mixture becomes colorless. It is then cooled to 0°, and the above diphenylamine which precipitates is filtered therefrom and washed with water. After drying the same under vacuum, 2.5 g of pure product, which melts at 167°, are obtained.

| Analysis | Calculated for $C_{16}H_{21}N_3O$ | Found | |
|---|---|---|---|
| C% | 70.82 | 70.82 | 70.75 |
| H% | 7.80 | 7.89 | 7.76 |
| N% | 15.49 | 15.63 | 15.47 |

0.5 g of this diphenylamine thus obtained is introduced into 10 cc of a hydrochloric solution ($d$ = 1.19) at 25°. After stirring five minutes, the insoluble 4-hydroxy 3,3',5,5'-tetramethyl 2',4'-diamino diphenylamine dihydrochloride is filtered. This product is then first washed with hydrochloric acid $d$ = 1.19, and subsequently with a little acetone. Thereafter the product is dried for three days under a nitrogen atmosphere. It melts with decomposition at 225°.

Molecular weight calculated for $C_{16}H_{12}N_3O.2HCl$ = 344
Molecular weight found by potentiometric determination in water with a 0.1 N soda solution = 344

EXAMPLE 9

4-hydroxy 3-methyl 2',4'-diamino diphenylamine is prepared in accordance with the following reaction:

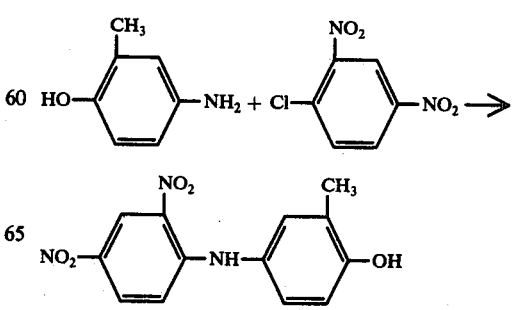

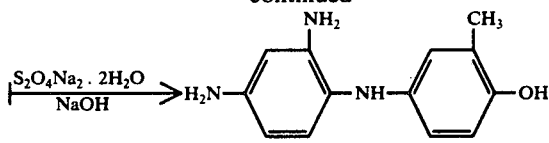

1st Phase:
Preparation of 4-hydroxy 3-methyl 2',4'-dinitro diphenylamine

Into 100 cc of absolute ethyl alcohol there are introduced, on the one hand, 0.05 mole (6.15 g) of 2-methyl 4-amino phenol and, on the other hand, 0.05 mole (10.13 g) of 2,4-dinitro chlorobenzene and 6.15 g of molten sodium acetate. The resulting mixture is brought to reflux and maintained there for 5 hours with stirring, after which it is filtered while boiling to eliminate inorganic salts. After cooling the alcohol filtrate in ice, the 4-hydroxy 3-methyl 2',4'-dinitro diphenylamine, which has crystallized, is filtered therefrom. This dinitro diphenylamine after washing with water, recrystallized, in alcohol and drying under vacuum, melts at 176°.

| Analysis | Calculated for $C_{13}H_{11}N_3O_5$ | Found | |
|---|---|---|---|
| C% | 53.98 | 53.86 | 54.09 |
| H% | 3.83 | 4.08 | 3.94 |
| N% | 14.53 | 14.43 | 14.51 |

2nd Phase:
Preparation of 4-hydroxy 3-methyl 2',4'-diamino diphenylamine 0.0714 mole (20 g) of sodium hydrosulfite of 75% purity is dissolved in 225 cc or normal soda solution. To this solution there is added gradually, with good stirring, while keeping the temperature in the vicinity of 55°, 0.0138 mole (4 g) of the dinitro diphenylamine obtained in the first phase. When the addition is completed and the reaction mixture is colorless, it is cooled. Then acetic acid is added to it until the pH equals 7.5, thereby precipitating the above diphenylamine which is then filtered, washed with dimethylfor...

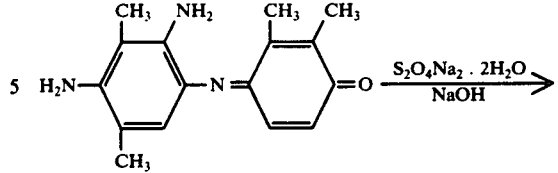

To 160 cc of a 1.25 N soda solution containing in solution 0.05 mole (14 g) of sodium hydrosulfite of 75% purity there is added, gradually, with good stirring, while keeping the reaction mixture in the vicinity of 30°, 0.02 mole (5.38 g) of N-[(2',4'-diamino 3',5'-dimethyl) phenyl] 2,3-dimethyl benzoquinoneimine partially dissolved in 50 cc of 95° ethanol. When the addition is completed and the reaction mixture is colorless, it is rapidly filtered under nitrogen and, after neutralizing with acetic acid, the above diphenylamine, which has precipitated, is filtered therefrom. After washing, the said diphenylamine with water and drying it under vacuum at 80° for 5 hours, the product (4.8 g) melts at 166°.

Molecular weight calculated for $C_{16}H_{21}N_3O$ = 271
Molecular weight found by potentiometric determination in acetic acid by perchloric acid = 274

| Analysis | Calculated for $C_{16}H_{21}N_3O$ | Found | |
|---|---|---|---|
| C % | 70.82 | 70.94 | 70.57 |
| H % | 7.80 | 7.72 | 7.78 |
| N % | 15.49 | 15.31 | 15.47 |

EXAMPLE 11

4-hydroxy 3-methyl 2'-amino N,N-dimethylamino-4 diphenylamine is prepared in accordance with the following reaction:

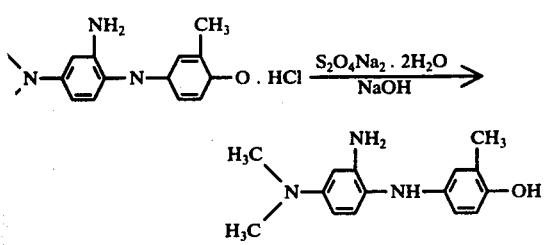

nole (7 g) of sodium hydrosulfite of 75% purity ed in 80 cc of a 1.25 N soda solution. To this solution there is added gradually, with stir-
keeping the temperature in the vicinity of mole (2.91 g) of N-[(2'-amino 4'-dimephenyl] 3-methyl benzoquinoneimine hy- in solution in 30 cc of water. When the mpleted, the reaction mixture is allowed to ly colorless. Then acetic acid is added to pitate the above diphenylamine which is inder nitrogen, washed with water and icuum for 5 hours at 80°. 2.35 g of the pure diphenylamine which melts at 187° are thus obtained.

Molecular weight calculated for $C_{15}H_{19}N_3O = 257$
Molecular weight found by potentiometric determination in acetic acid by perchloric acid = 258

| Analysis | Calculated for $C_{15}H_{19}N_3O$ | Found | |
|---|---|---|---|
| C % | 70.00 | 70.30 | 70.24 |
| H % | 7.44 | 7.37 | 7.32 |
| N % | 16.33 | 16.49 | 16.29 |

EXAMPLE 12

4-hydroxy 3,3',5'-trimethyl 2',4'-diamino diphenylamine is prepared in accordance with the following reaction:

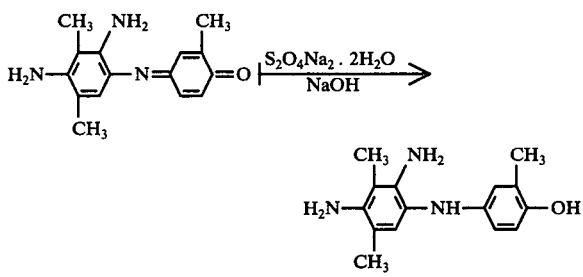

0.0175 mole (4.9 g) of sodium hydrosulfite of 75% purity is dissolved in 50 cc of 1.25 N soda solution. To this resulting solution there is added gradually, with stirring, while keeping the temperature in the vicinity of 30°, 0.007 mole (1.78 g) of N-[(2',4'-diamino 3',5'-dimethyl) phenyl] 3-methyl benzoquinoneimine in 10 cc of 95° C ethanol. When the addition is completed, the reaction mixture very rapidly becomes colorless. Then acetic acid is added to it until neutralization thereby precipitating the above diphenylamine which is then filtered under nitrogen, washed with water and dried under vacuum for 5 hours at 80°. 0.84 g of the pure product, which melts at 141°, is thus obtained.

| Analysis | Calculated for $C_{15}H_{19}N_3O$ | Found | |
|---|---|---|---|
| C % | 70.00 | 69.86 | 69.73 |
| H % | 7.44 | 7.37 | 7.39 |
| N % | 16.33 | 16.28 | 16.37 |

EXAMPLE 13

N-[(6'-amino 1'-oxa 4'aza 1', 2',3',4'-tetrahydro) 7'-naphthyl] 4-amino 2-methyl phenol is prepared in accordance with the following reaction:

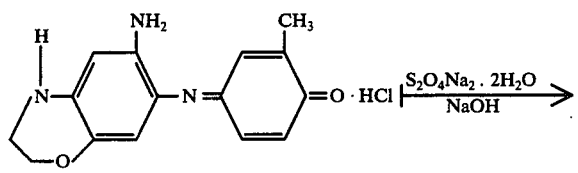

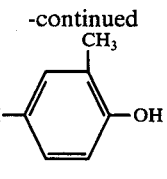

0.05 mole (14 g) of sodium hydrosulfite of 75% purity is dissolved in 160 cc of a 1.25 N soda solution. To this resulting solution there is added gradually, with stirring, while keeping the temperature in the vicinity of 30°, 0.02 mole (6.11 g) of N-[(6'-amino 1'-oxa 4'-aza 1',2',3',4'-tetrahydro) 7'-naphthyl] 3-methyl benzoquinoneimine hydrochloride dissolved in 30 cc of ethanol and 10 cc of water. When the addition is completed, the reaction mixture is colorless. Then acetic acid is added to it to pH 7 thereby precipitating the above diphenylamine which is then filtered under nitrogen, washed with water and dried under vacuum at 80° for 5 hours. 5.42 g of pure product, which melts at 210°, are thus obtained.

Molecular weight calculated for $C_{15}H_{17}N_3O_2 = 271$
Molecular weight found by potentiometric determination in acetic acid by perchloric acid = 271

| Analysis | Calculated for $C_{15}H_{17}N_3O_2$ | Found | |
|---|---|---|---|
| C% | 66.43 | 66.21 | 65.98 |
| H% | 6.27 | 6.24 | 6.33 |
| N% | 15.49 | 15.30 | 15.52 |

EXAMPLE 14

4-hydroxy 3,5-dimethyl 2'-amino 4'-dimethylamino diphenylamine is prepared in accordance with the following reaction:

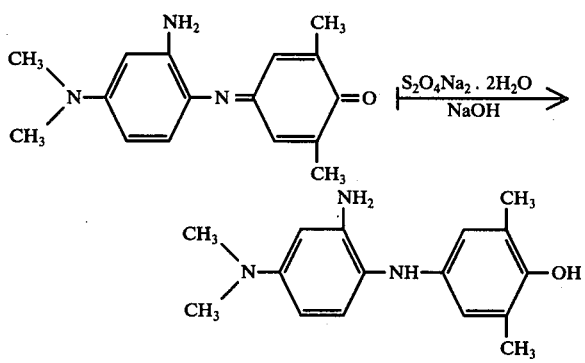

0.0175 mole (4.9 g) of sodium hydrosulfite of 75% purity is dissolved in 80 cc of a 1.26 N soda solution. To this resulting solution there is gradually added, with stirring and while keeping the temperature in the vicinity of 35°, 0.007 mole (1.88 g) of N-[(2'-amino 4'-dimethylamino) phenyl] 3,5-dimethyl benzoquinoneimine in 20 cc of 95° ethanol. When the addition is completed, the stirring is kept up for about 30 minutes until total loss of color of the reaction mixture. The acetic acid is added to pH 7 and the above diphenylamine precipitates. The thus recovered diphenylamine is then filtered, washed with water and dried under vacuum. 1.33 g of pure product, which melts at 148°, are obtained.

Molecular weight calculated for $C_{16}H_{21}N_3O = 271$

Molecular weight found by potentiometric determination in acetic acid by perchloric acid = 273

| Analysis | Calculated for $C_{16}H_{21}N_3O$ | Found | |
|---|---|---|---|
| C% | 70.82 | 70.35 | 70.43 |
| H% | 7.80 | 7.77 | 7.69 |
| N% | 15.49 | 15.37 | 15.54 |

EXAMPLE 15

4-hydroxy 2,5'-dimethyl 2',4'-diamino diphenylamine is prepared in accordance with the following reaction:

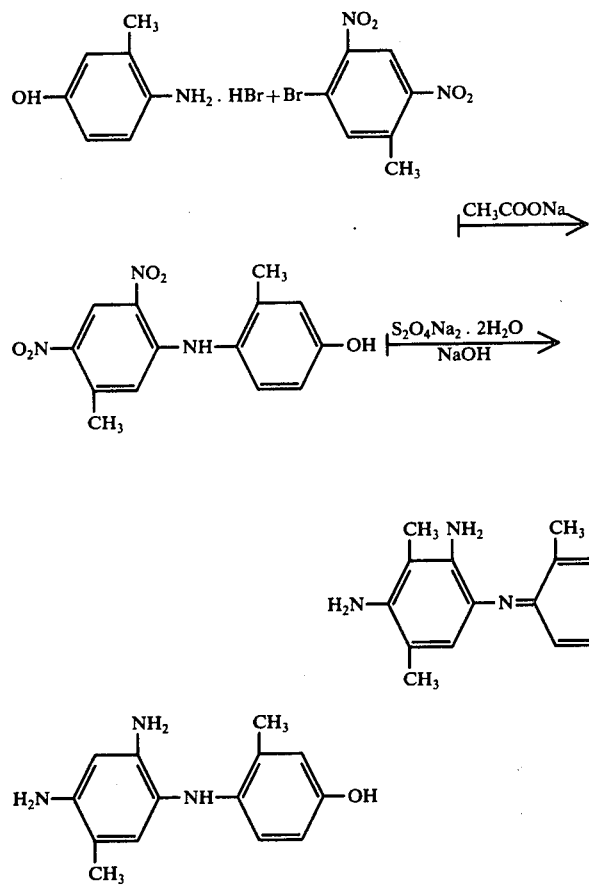

1st phase. Preparation of 4-hydroxy 2,5'-dimethyl 2',4'-dinitro diphenylamine

Into 40 cc of absolute ethanol there are introduced, on the one hand, 0.005 mole (1.02 g) of 3-methyl 4-amino phenol hydrobromide, and, on the other hand, 0.005 mole (1.3 g) of 2,4-dinitro 5-bromo toluene and 0.9 g of molten sodium acetate. The resulting mixture is brought to reflux for 5 hours with stirring, and then filtered hot to eliminate the inorganic salts. 40 cc of water are added and then cooled to 0° for 1 hour thereby precipitating the above dinitro diphenylamine which is then filtered, 1.2 g of 4-hydroxy 2,5'-dimethyl 2',4'-dinitro yielding 1.2 g of the same, which, after recrystallization in an ethanol-water mixture and drying under vacuum melts at 168°.

| Analysis | Calculated for $C_{14}H_{13}N_3O_5$— | Found | |
|---|---|---|---|
| C% | 55.44 | 55.54 | 55.66 |
| H% | 4.29 | 4.45 | 4.36 |

| Analysis | Calculated for $C_{14}H_{13}N_3O_5$— | Found | |
|---|---|---|---|
| N% | 13.86 | 13.53 | 13.62 |

2nd phase. Preparation of 4-hydroxy 2,5'-dimethyl 2',4'-diamino diphenylamine.

0.02 mole (4.64) of sodium hydrosulfite of 75% purity is dissolved in 35 cc of normal soda solution. To this solution there is gradually added, with good stirring, while keeping the temperature in the vicinity of 55°, 0.003 mole (1 g) of the dinitro diphenylamine previously obtained in the first phase above. When the addition is completed and the reaction mixture is colorless, it is cooled. Then acetic acid is added to it until neutralization to precipitate the above diphenylamine which is then filtered, washed with water and dried under vacuum. 0.4 g of pure product, which melts at 153°, is thus obtained.

| Analysis | Calculated for $C_{14}H_{17}N_3O \cdot 0.5 H_2O$ | Found | |
|---|---|---|---|
| C% | 66.63 | 67.00 | 66.98 |
| H% | 7.20 | 7.29 | 7.21 |
| N% | 16.65 | 16.52 | 16.57 |

EXAMPLE 16

4-hydroxy 2,3',5'-trimethyl 2',4'-diamino diphenylamine and its dihydrochloride, monohydrate are prepared as follows:

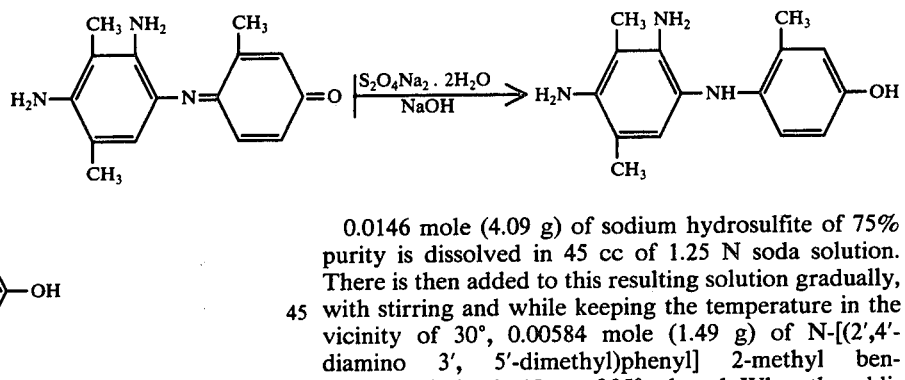

0.0146 mole (4.09 g) of sodium hydrosulfite of 75% purity is dissolved in 45 cc of 1.25 N soda solution. There is then added to this resulting solution gradually, with stirring and while keeping the temperature in the vicinity of 30°, 0.00584 mole (1.49 g) of N-[(2',4'-diamino 3', 5'-dimethyl)phenyl] 2-methyl benzoquinoneimine in 10 cc of 95° ethanol. When the addition is completed, the reaction mixture is allowed to become colorless. Acetic acid is then added until neutrality to precipitate the above diphenylamine which is then filtered under nitrogen, washed with water and recrystallized in a dimethylformamidewater mixture. 0.90 g of pure product, which melts at 204°, is obtained.
Molecular weight calculated for $C_{15}H_{19}N_3O$ = 257
Molecular weight found by potentiometric determination in acetic acid by perchloric acid = 255

| Analysis | Calculated for $C_{15}H_{19}N_3O$ | Found | |
|---|---|---|---|
| C% | 70.00 | 70.15 | 70.37 |
| H% | 7.44 | 7.44 | 7.34 |
| N% | 16.33 | 16.48 | 16.26 |

0.20 g of the diphenylamine thus obtained is dissolved in 5 cc of hydrochloric acid (d = 1.19) at 25°. The hydrochloric solution is cooled to −10°. The 4-hydroxy 2,3',5'-trimethyl 2',4'-diamino diphenylamine dihydrochloride monohydrate crystallizes and it is filtered and dried under a nitrogen atmosphere. This resulting product melts with decomposition at 214°. Molecular weight calculated for $C_{15}H_{19}N_3O \cdot H_2O \cdot 2HCl = 348$
Molecular weight found by potentiometric determination in water, with 0.1 N soda solution = 352

EXAMPLE 17

4-Hydroxy 3-chloro 2',4'-diamino 5'-methoxy diphenylamine is prepared in accordance with the following reaction:

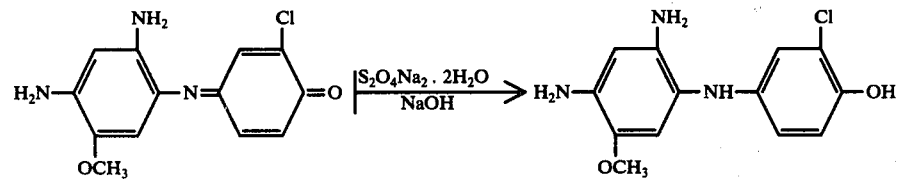

0.025 mole (7 g) of sodium hydrosulfite of 75% purity is dissolved in 75 cc of 1.25 N soda solution. To this resulting solution there is added gradually, with stirring and while keeping the temperature in the vicinity of 30°, 0.01 mole (2.77 g) of N-[(2',4'-diamino 5'-methoxy)-phenyl]3-chloro benzoquinoneimine in 15 cc of 95° ethanol. When the reaction mixture is colorless, acetic acid is added to it to neutrality thereby precipitating the above diphenylamine which is then filtered under nitrogen, washed with water and dried under vacuum at 80° for 5 hours. 2.50 g of pure product, which melts at 195°, are thus obtained. Molecular weight calculated for $C_{13}H_{14}N_3O_2Cl = 279.5$
Molecular weight found by potentiometric determination in acetic acid by perchloric acid = 278

| Analysis | Calculated for $C_{13}H_{14}N_3O_2Cl$ | Found | |
|---|---|---|---|
| C% | 55.82 | 55.69 | 55.77 |
| H% | 5.04 | 5.08 | 5.10 |
| N% | 15.02 | 15.18 | 15.25 |

EXAMPLE 18

4-hydroxy 2-chloro 2',4'-diamino 5'-methoxy diphenylamine is insert prepared in accordance with the following reaction:

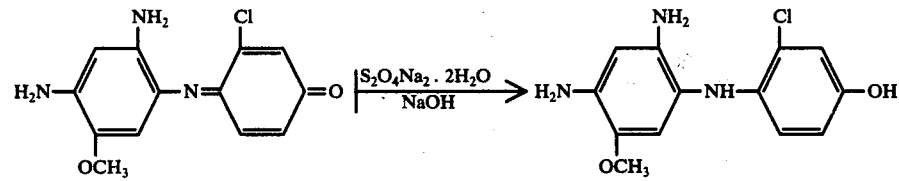

0.025 mole (7 g) of sodium hydrosulfite of 75% purity is dissolved in 72 cc of 1.25 N soda solution. To this resulting solution, there is gradually added, with stirring, and while keeping the temperature in the vicinity of 30°, 0.01 mole (2.77 g) of N-[(2',4'-diamino 5'-methoxy) phenyl] 2-chloro benzoquinoneimine in 15 cc of 95° ethanol. When the addition is completed, the reaction mixture is allowed to become completely colorless. Acetic acid is then added to it until neutrality thereby precipitating the above diphenylamine which is then filtered under nitrogen, washed with water and dried 3 days under vacuum on $P_2O_5$. 2.1 g of pure product, which melts at 137° are obtained.
Molecular weight calculated for $C_{13}H_{14}N_3O_2Cl = 279.5$
Molecular weight found by potentiometric determination in acetic acid by perchloric acid = 281

| Analysis | Calculated for $C_{13}H_{14}N_3O_2Cl$ | Found | |
|---|---|---|---|
| C% | 55.82 | 55.97 | 55.69 |
| H% | 5.04 | 4.92 | 4.94 |
| N% | 15.02 | 15.20 | 14.92 |

EXAMPLE 19

4-hydroxy 3,6,3',5'-tetramethyl 2',4'-diamino diphenylamine is prepared as follows:

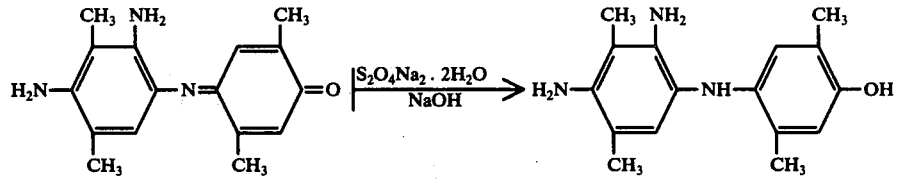

0.0167 mole (4.62 g) of sodium hydrosulfite of 75% purity is dissolved in 48 cc of a 1.25 N soda solution. To this resulting solution there is added gradually, with stirring, while keeping the temperature in the vicinity of 30°, 0.0067 mole (1.80 g) of N-[(2',4'-diamino 3',5'-dimethyl) phenyl] 3,6-dimethyl benzoquinoneimine. When the addition is completed, the reaction mixture very rapidly becomes colorless and it is then neutralized to a pH of 7.5 with carbon dioxide gas. The above diphenylamine precipitates and is filtered therefrom, after which it is washed with water, recrystallized in a dimethylformamide-water mixture and dried for 2 days on $P_2O_5$. 1 g of the pure product, which melts at 153°, is thus obtained.
Molecular weight calculated for $C_{16}H_{21}N_3O = 271$ Molecular weight found by potentiometric determination in acetic acid by perchloric acid = 274

| Analysis | Calculated for C₁₆H₂₁N₃O | Found | |
|---|---|---|---|
| C% | 70.82 | 70.83 | 70.77 |
| H% | 7.80 | 7.80 | 7.93 |
| N% | 15.49 | 15.73 | 15.54 |

EXAMPLE 20

4-hydroxy 2-methyl 2'-acetylamino 4'-amino diphenylamine is insert prepared in accordance with the following reaction:

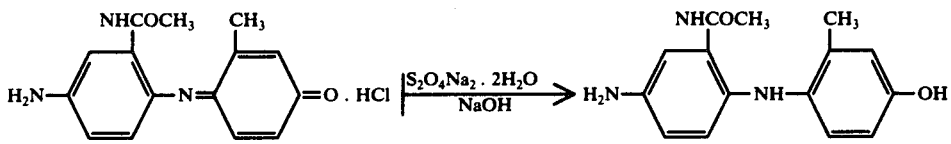

0.025 mole of sodium hydrosulfite of 75% purity (7 g) dissolved in 72 cc of 1.25 N soda solution. To this resulting solution there is gradually added, with stirring, while keeping the temperature in the vicinity of 30°, 0.01 mole (3.05 g) of N-[(2'-acetylamino 4'-amino) phenyl] 2-methyl benzoquinoneimine hydrochloride dissolved in 15 cc of ethyl alcohol and 10 cc of water. The reaction mixture very quickly becomes colorless. Acetic acid is then added to it to neutralize the same, thereby precipitating the above diphenylamine which is then filtered, washed with water and dried under vacuum. After recrystallization in a dimethylformamide-water mixture and drying under vacuum, the product melts at 210°.

| Analysis | Calculated for C₁₅H₁₇N₃O₂ | Found | |
|---|---|---|---|
| C% | 66.40 | 65.98 | 66.12 |
| H% | 6.32 | 6.27 | 6.35 |
| N% | 15.49 | 15.57 | 15.68 |

EXAMPLE 21

4-hydroxy 3,5-dimethyl 2'-acetylamino 4'-dimethylamino diphenylamine is prepared in accordance with the following reaction:

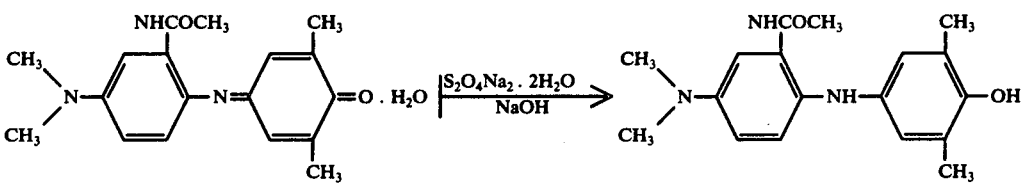

0.025 mole (7 g) of sodium hydrosulfite is dissolved in 75 cc of a 1.25 N soda solution. To this resulting solution there is gradually added, with stirring and while keeping the temperature in the vicinity of 30°, 0.01 mole (3.29 g) of N-[(2'-acetylamino 4'-dimethylamino) phenyl] 3,5-dimethyl benzoquinoneimine monohydrate in 15 cc of 95° ethanol. When the addition is completed, the mixture is allowed to become completely colorless. Acetic acid is then added to it until neutrality thereby precipitating the above diphenylamine which is then filtered, washed with water, recrystallized in a dimethylformamide-water mixture, and dried for 5 hours under vacuum, yielding 1.83 g of pure product, melting at 197°.

Molecular weight calculated for $C_{18}H_{23}N_3O_2$ = 313
Molecular weight found by potentiometric determination in acetic acid by perchloric acid = 309

| Analysis | Calculated for C₁₈H₂₃N₃O₂ | Found | |
|---|---|---|---|
| C% | 69.01 | 68.86 | 68.74 |
| H% | 7.35 | 7.42 | 7.39 |
| N% | 13.41 | 13.39 | 13.30 |

EXAMPLE 22

4-hydroxy 3-chloro 2'-acetylamino 4'-amino 5'-methyl diphenylamine is prepared in accordance with the following reaction:

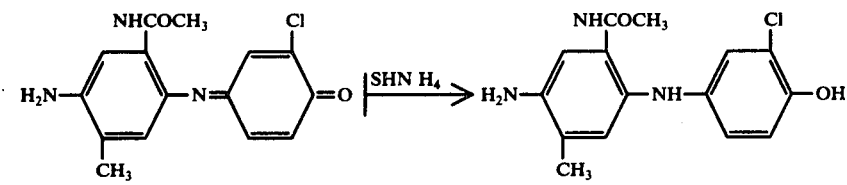

0.0025 mole (0.759 g) of N-[2'-acetylamino 4'-amino 5'-methyl) phenyl]3-chloro benzoquinoneimine is dissolved in 45 cc of water and 30 cc of ethyl alcohol. To this dilute alcohol solution there is added, drop by drop, with stirring and at 250°, 2 cc of an aqueous ammonia solution at 16° Be, previously saturated with sulfurated hydrogen. After 30 minutes, the reaction mixture is colorless. It is then cooled to 0°, and the above diphenylamine precipitates which, in turn, is filtered and washed with water. After recrystallization in a diethylformamide-water mixture, 0.40 g of pure product, which melts at 206°, is obtained.

Molecular weight calculated for $C_{15}H_{16}N_3O_2Cl$ = 305.5
Molecular weight found by potentiometric determination in acetic acid by perchloric acid = 308

| Analysis | Calculated for C$_{15}$H$_{16}$N$_3$O$_2$Cl | Found | |
|---|---|---|---|
| C% | 58.92 | 59.11 | 59.07 |
| H% | 5.27 | 5.33 | 5.29 |
| N% | 13.74 | 13.55 | 13.68 |

EXAMPLE 23

N-[(6'-hydroxy 1'-oxa 4'-aza 1',2',3',4'-tetrahydro) 7'-naphthyl] 4-amino 2-methyl phenyl is prepared in accordance with the following reaction:

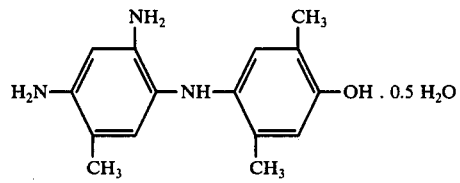

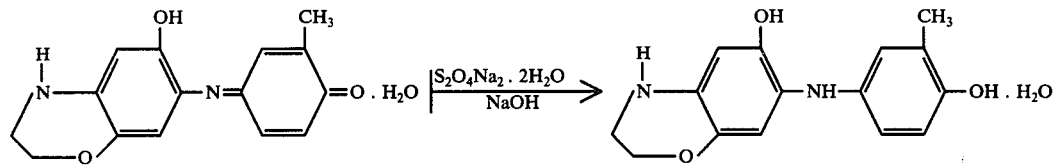

0.05 mole (14 g) of sodium hydrosulfite of 75% purity is dissolved in 145 cc of 1.25 N soda solution. To this resulting solution there is gradually added, with stiring and while keeping the temperature in the vicinity of 30°, 0.02 mole (5.76 g) of N-[(6'-hydroxy 1'-oxa 4'-aza 1',2',3',4'-tetrahydro) 7'-naphthyl] 3-methyl benzoquinoneimine monohydrate in 30 cc of ethanol. When the addition is completed, the reaction mixture very rapidly becomes colorless. Acetic acid is then added to it until neutrality thereby precipitating the above diphenylamine which is then filtered under nitrogen, washed in water and dried under vacuum for 5 hours at 80°. 4.30 g of pure product in monohydrate form, which melts at 194°, are thus obtained.

| Analysis | Calculated for C$_{15}$H$_{16}$N$_2$O$_3$ . H$_2$O | Found | |
|---|---|---|---|
| C% | 62.07 | 61.73 | 61.96 |
| H% | 6.20 | 6.31 | 6.25 |
| N% | 9.65 | 9.42 | 9.68 |

EXAMPLE 24

Third method for preparing 4-hydroxy 2,6,3',5'-tetramethyl 2',4'-diamino diphenylamine already described in Examples 6 and 7 is as follows 0.00372 mole (1 g) of N-[(2',4'-diamino 3',5'-dimethyl) phenyl] 2,6-dimethyl benzoquinoneimine is dissolved in 100 cc of absolute ethyl alcohol. Then palladium on barium sulfate (5% Pd/Ba SO$_4$) is added as the catalyst and the product is reduced in the usual way by hydrogen at ambient pressure. After 15 minutes, the alcohol solution has become completely colorless. This solution is then filtered to recover the catalyst and it is concentrated under vacuum and nitrogen up to 15 cc. 40 cc of water are then added and the above diphenylamine which is filtered and dried under vacuum exhibits a melting point of 251° and does not give a lowering of the melting point when used in mixture with the products prepared according to the processes described in Examples 6 and 7.

EXAMPLE 25

4-hydroxy 3,6,5'-trimethyl 2',4'-diamino diphenylamine is prepared as follows:

1st phase — Preparation of 4-hydroxy 3,6,5'-trimethyl 2',4'-dinitro diphenylamine Into 300 cc of absolute ethanol there are introduced, on the one hand, 0.04 mole (10.44 g) of 2,4-dinitro 5-bromo toluene, and, on the other hand, 0.04 mole (5.48 g) of 2,5-dimethyl 4amino phenol and 4.1 g of molten sodium acetate. The resulting mixture is heated to reflux for 5 hours with stirring and filtered hot to eliminate the inorganic salts. 300 cc of water are then added and the mixture cooled to 0° thereby precipitating 11 g of 4-hydroxy 3, 6,5'-trimethyl 2',4'-dinitro diphenylamine which are filtered and which, after recrystallization in ethanol, melt at 174°.

| Analysis | Calculated for C$_{15}$H$_{15}$N$_3$O$_5$ | Found | |
|---|---|---|---|
| C% | 56.78 | 56.87 | 56.99 |
| H% | 4.77 | 4.86 | 4.92 |
| N% | 13.24 | 13.42 | 13.26 |

Second phase — Preparation of 4-hydroxy 3,6,5'-trimethyl 2',4'-diamino diphenylamine 0.0714 mole (20 g) of sodium hydrosulfite of 75% purity is dissolved in 300 cc of a normal soda solution. To this resulting solution there is added gradually, with good stirring, while keeping the temperature in the vicinity of 55°, 0.01 mole (3.2 g) of the dinitro derivative obtained in the first phase, as described above. When the addition is completed and the reaction mixture is colorless, it is cooled and then neutralized with acetic acid to precipitate the above diphenylamine. After filtering, washing with water and drying under vacuum at 80° for 5 hours, the product melts at 214°.

Molecular weight calculated for C$_{15}$H$_{19}$N$_3$O · 0.5 H$_2$O = 266

Molecular weight found by potentiometric determination in acetic acid by perchloric acid = 267

| Analysis | Calculated for C$_{15}$H$_{19}$N$_3$O . 0.5 H$_2$O | Found | |
|---|---|---|---|
| C% | 67.65 | 67.94 | 67.86 |
| H% | 7.51 | 7.57 | 7.54 |
| N% | 15.78 | 16.00 | 15.83 |

EXAMPLE 26

4-hydroxy 2,3-dimethyl 5'-methoxy 2',4'-diamino diphenylamine is prepared as follows:

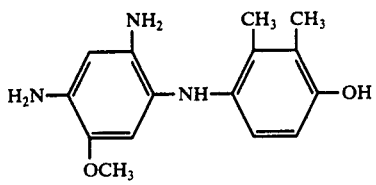

1st phase — Preparation of 4-hydroxy 2,3-dimethyl 5'-methoxy 2',4'-dinitro diphenylamine Into 60 cc of absolute ethanol there are introduced, on the one hand, 0.03 mole (6.97 g) of 2,4-dinitro-6-methoxy chlorobenzene and, on the other hand, 0.03 mole (4.11 g) of 2,3-dimethyl 4-amino phenol and 3.69 g of molten sodium acetate. The resulting mixture is heated to reflux for 5 hours with stirring. After cooling, 4-hydroxy 2,3-dimethyl 5'-methoxy 2',4'-dinitro diphenylamine which precipitates therefrom, is filtered and washed with water to eliminate the inorganic salts. After recrystallization in ethyl alcohol, the product melts at 234°.

| Analysis | Calculated for $C_{15}H_{15}N_3O_6$ | Found | |
|---|---|---|---|
| C% | 54.05 | 54.21 | 54.17 |
| H% | 4.54 | 4.59 | 4.43 |
| N% | 12.61 | 12.47 | 12.56 |

2nd phase — Preparation of 4-hydroxy 2,3-dimethyl 5'-methoxy 2',4'-diamino diphenylamine 0.003 mole (1 g) of the above dinitro derivative obtained in the first phase is dissolved in 80 cc of ethyl acetate. 0.2 g of palladium on carbon (10% Pd on C) is added and the product is reduced by hydrogen at ambient pressure. The solution is filtered to recover the catalyst. After addition of petroleum ether, 4-hydroxy 2,3-dimethyl 5'-methoxy 2',4'-diamino diphenylamine crystallizes, which is then filtered and dried under vacuum for several days. This product melts at 195°.

| Analysis | Calculated for $C_{15}H_{19}N_3O_2$ | Found | |
|---|---|---|---|
| C% | 65.91 | 65.73 | 65.89 |
| H% | 7.01 | 7.02 | 7.12 |
| N% | 15.37 | 15.29 | 15.23 |

EXAMPLE 27

The following hair dye composition is prepared:

| | |
|---|---|
| Dye of Example 1 | 0.1 g |
| Ethyl alcohol, 96° titer | 20 g |
| Water, q.s.p. | 100 g |
| Ammonia at 22° Be, q.s.p pH 10 | |

This hair dye composition when applied for 20 minutes to 95% naturally white hair, imparts thereto an intense violine shade after rinsing and shampooing.

EXAMPLE 28

The following hair dye composition is prepared:

| | |
|---|---|
| Dye of Example 10 | 0.1 g |
| Ethyl alcohol, 96° titer | 20 g |
| Water, q.s.p. | 100 g |
| Ammonia at 22° Be, q.s.p. pH 10 | |

This hair dye composition when applied for 20 minutes to bleached hair, imparts thereto, after rinsing and shampooing, a very luminous intense parme shade.

EXAMPLE 29

The following hair dye composition is prepared:

| | |
|---|---|
| Dye of Example 5 | 0.1 g |
| Ethyl alcohol, 96° titer | 30 g |
| Water, q.s.p. | 100 g |
| Ammonia at 22° Be, q.s.p. pH 10 | |

This hair dye composition when applied for 20 minutes to bleached hair, imparts thereto, after rinsing and shampooing, a silvery blue gray shade.

EXAMPLE 30

The following hair dye composition is prepared:

| | |
|---|---|
| Dye of Example 6 | 0.1 g |
| Isopropyl alcohol, 96° titer | 40 g |
| Water, q.s.p | 100 g |
| Ammonia at 22° Be, q.s.p. pH 9.5 | |

This hair dye composition when applied for 20 minutes to 95% naturally white hair, imparts thereto, after rinsing and shampooing, an ash beige shade with pink glints.

EXAMPLE 31

The following hair dye composition is prepared:

| | |
|---|---|
| Dye of Example 3 | 0.15 g |
| Ethyl alcohol, 96° titer | 30 g |
| Water, q.s.p. | 100 g |
| The pH of the solution is 8. | |

The pH of the solution is 8.

This hair dye composition when applied for 15 minutes to 95% naturally white hair, imparts thereto, after rinsing and shampooing, an intense purple violet shade.

EXAMPLE 32

The following hair dye composition is prepared:

| | |
|---|---|
| Dye of Example 4 | 0.085 g |
| Ethyl alcohol, 96° titer | 20 g |
| Water, q.s.p. | 100 g |
| Ammonia at 22° Be, q.s.p. pH 9 | |

This hair dye composition when applied for 20 minutes to 95% naturally white hair, imparts thereto, after rinsing and shampooing, a slightly violet red shade with golden glints.

EXAMPLE 33

The following hair dye composition is prepared:

| | |
|---|---|
| Dye of Example 6 | 0.1 g |
| Ethyl alcohol, 96° titer | 20 g |
| Water, q.s.p. | 100 g |
| Ammonia at 22° Be, q.s.p. pH 10 | |

This hair dye composition when applied for 20 minutes to bleached hair, imparts thereto, after rinsing and shampooing, a very intense purple violet shade.

EXAMPLE 34

The following hair dye composition is prepared:

| | |
|---|---|
| Dye of Example 8 (in dihydrochloride form) | 0.165 g. |
| Ethyl alcohol, 96° titer | 30 g |
| Water, q.s.p. | 100 g |
| Ammonia at 22° Be, q.s.p. pH 9 | |

This hair dye composition when applied for 15 minutes to 95% naturally white hair, imparts thereto, after rinsing and shampooing, a very luminous mauve shade with pink glints.

EXAMPLE 35

The following hair dye composition is prepared:

| | |
|---|---|
| Dye of Example 2 (in dihydrochloride, monohydrate form) | 0.15 g |
| Ethyl alcohol, 96° titer | 40 g |
| Water, q.s.p. | 100 g |
| Ammonia at 22° Be, q.s.p. pH 9.5 | |

This hair dye composition when applied for 20 minutes to bleached hair, imparts thereto, after rinsing and shampooing, a silvery turquoise blue shade.

EXAMPLE 36

The solution of Example 35 is applied for 20 minutes to 95% naturally white hair. After rinsing and shampooing, a very luminous silver gray is obtained.

EXAMPLE 37

The following hair dye composition is prepared:

| | |
|---|---|
| Dye of Example 11 | 0.085 g |
| Ethyl alcohol, 96° titer | 30 g |
| Water, q.s.p. | 100 g |
| 1% lactic acid solution, q.s.p. pH 5.5 | |

This hair dye composition when applied for 20 minutes to bleached hair, imparts thereto, after rinsing and shampooing, a very strong violet shade.

EXAMPLE 38

The following hair dye composition is prepared:

| | |
|---|---|
| Dye of Example 9 | 0.1 g |
| Ethyl alcohol, 96° titer | 25 g |
| Water, q.s.p. | 100 g |
| 1% lactic acid solution, q.s.p. pH 7 | |

This hair dye composition when applied for 20 minutes to 95% naturally white hair, imparts thereto, after rinsing and shampooing, an ash blond shade with mauve glints.

EXAMPLE 39

The following hair dye composition is prepared:

| | |
|---|---|
| Dye of Example 15 | 0.1 g |
| Isopropyl alcohol, 96° titer | 30 g |
| Water, q.s.p. | 100 g |
| Ammonia at 22° Be, q.s.p. pH 10 | |

This hair dye composition when applied for 15 minutes to 95% naturally white hair, imparts thereto, after rinsing and shampooing, a very luminous cyclamen shade.

EXAMPLE 40

The following hair dye composition is prepared:

| | |
|---|---|
| Dye of Example 19 | 0.065 g |
| Ethyl alcohol, 96° titer | 20 g |
| Water, q.s.p. | 100 g |
| 1% lactic acid solution, q.s.p. pH 7.5 | |

This hair dye composition when applied for 20 minutes to 95% naturally white hair, imparts thereto, after rinsing and shampooing, a pearly glycine shade.

EXAMPLE 41

The following hair dye composition is prepared:

| | |
|---|---|
| Dye of Example 13 | 0.15 g |
| Ethyl alcohol, 96° titer | 50 g |
| Water, q.s.p. | 100 g |
| 1% lactic acid solution, q.s.p. pH 7 | |

This hair dye composition when applied for 20 minutes to 95% naturally white hair, imparts thereto, after rinsing and shampooing, an iridescent violet pink shade.

EXAMPLE 42

The following hair dye composition is prepared:

| | |
|---|---|
| Dye of Example 16 | 0.03 g |
| Ethyl alcohol, 96° titer | 30 g |
| Water, q.s.p. | 100 g |
| 1% lactic acid solution, q.s.p. pH 6 | |

This hair dye composition when applied for 30 minutes to bleached hair, imparts thereto, after rinsing and shampooing, a cyclamen coloring.

EXAMPLE 43

The following hair dye composition is prepared:

| | |
|---|---|
| Dye of Example 1 | 0.005 g |
| Ethyl alcohol, 96° titer | 20 g |
| Water, q.s.p. | 100 g |
| 1% lactic acid solution, q.s.p. pH 6.5 | |

This hair dye composition when applied for 20 minutes to bleached hair, imparts thereto, after rinsing and shampooing, a bright pink shade with golden glints.

EXAMPLE 44

The following hair dye composition is prepared:

| | |
|---|---|
| Dye of Example 12 | 0.04 g |
| Ethyl alcohol, 96° titer | 30 g |
| Water, q.s.p. | 100 g |
| 1% lactic acid solution, q.s.p. pH 7.5 | |

This hair dye composition when applied for 25 minutes to 95% naturally white hair, imparts thereto, after rinsing and shampooing, a pearly rose shade.

EXAMPLE 45

The following hair dye composition is prepared:

| | |
|---|---|
| Dye of Example 17 | 0.1 g |

| | |
|---|---|
| Butylglycol | 5 g |
| Lauryl alcohol oxyethylenated with 10.5 moles of ethylene oxide | 5 g |
| Water, q.s.p. | 100 g |
| Ammonia at 22° Be, q.s.p. pH 9 | |

This hair dye composition when applied for 20 minutes to bleached hair, imparts thereto, after rinsing and shampooing, a golden blond shade with pink glints.

EXAMPLE 46

The following hair dye composition is prepared:

| | |
|---|---|
| Dye of Example 21 | 0.075 g |
| Ethyl alcohol, 96° titer | 30 g |
| Water, q.s.p. | 100 g |
| 1% lactic acid solution, q.s.p. pH 6 | |

This hair dye composition when applied for 20 minutes to bleached hair, imparts thereto, after rinsing and shampooing, a turquoise blue shade.

EXAMPLE 47

The following hair dye composition is prepared:

| | |
|---|---|
| Dye of Example 22 | 0.09 g |
| Ethyl alcohol, 96° titer | 30 g |
| Water, q.s.p. | 100 g |
| 1% lactic acid solution, q.s.p. pH 5.5 | |

This hair dye composition when applied for 20 minutes to bleached hair, imparts thereto, after rinsing and shampooing, a pale blue green shade with golden glints.

EXAMPLE 48

The following hair dye composition is prepared:

| | |
|---|---|
| Dye of Example 19 | 0.1 g |
| 4-hydroxy 2',4'-diamino 5'-methoxy diphenylamine dihydrochloride monohydrate | 0.02 g |
| Ethyl alcohol, 96° titer | 20 g |
| Water, q.s.p. | 100 g |
| Ammonia at 22° Be, q.s.p. pH 9 | |

This hair dye composition when applied for 20 minutes to natural medium brown hair, imparts thereto, after rinsing and shampooing, a dark brown coloring with violine glints.

EXAMPLE 49

The following hair-setting lotion composition is prepared:

| | |
|---|---|
| Dye of Example 17 | 0.05 g |
| Vinyl acetate-crotonic acid copolymer (90% vinyl acetate, 10% crotonic acid, molecular weight to 50,000) | 2 g |
| Ethyl alcohol, 96° titer | 50 g |
| Water, q.s.p. | 100 g |
| Ammonia at 22° Be, q.s.p. pH 6.5 | |

This hair-setting lotion when applied to bleached hair imparts thereto a golden blond shade with pink glints.

EXAMPLE 50

The following hair-setting lotion composition is prepared:

| | |
|---|---|
| Dye of Example 23 | 0.18 g |
| 4-hydroxy 2,4'-diamino 5-methyl diphenylamine dihydrochloride | 0.05 g |
| Vinyl acetate-crotonic acid copolymer (90% vinyl acetate, 10% crotonic acid - molecular weight 45,000 to 50,000) | 2 g |
| Ethyl alcohol, 96° titer | 50 g |
| Water, q.s.p. | 100 g |
| Ammonia at 22° Be, q.s.p. pH 8.5 | |

This hair-setting lotion when applied to bleached hair, imparts thereto a light golden bronze shade.

EXAMPLE 51

The following hair-setting lotion composition is prepared:

| | |
|---|---|
| Dye of Example 10 | 0.005 g |
| Vinyl acetate-crotonic acid copolymer (90% vinyl acetate, 10% crotonic acid, molecular weight 45,000 to 50,000) | 2 g |
| Isopropyl alcohol, 96° titer | 50 g |
| Water, q.s.p. | 100 g |
| Ammonia at 22° Be, q.s.p. pH 8 | |

This hair-setting lotion when applied to bleached hair, imparts thereto a pearly blond shade with pink glints.

EXAMPLE 52

The following hair-setting lotion composition is prepared:

| | |
|---|---|
| Dye of Example 19 | 0.055 g |
| Vinyl acetate-crotonic acid copolymer (90% vinyl acetate, 10% crotonic acid, molecular weight 45,000 to 50,000) | 2 g |
| Ethyl alcohol, 96° titer | 50 g |
| Water, q.s.p. | 100 g |
| Ammonia at 22° Be, q.s.p. pH 7 | |

This hair-setting lotion when applied to 95% naturally white hair, imparts thereto, a silvery gray shade with light mauve glints.

EXAMPLE 53

The following hair-setting lotion composition is prepared:

| | |
|---|---|
| Dye of Example 9 | 0.065 g |
| Vinyl acetate-crotonic acid copolymer (90% vinyl acetate, 10% crotonic acid - molecular weight 45,000 to 50,000) | 2 g |
| Ethyl alcohol, 96° titer | 50 g |
| Water, q.s.p. | 100 g |
| Ammonia at 22° Be, q.s.p. pH 8.5 | |

This hair setting lotion when applied to bleached hair, imparts thereto a pearly ash blond shade.

EXAMPLE 54

The following hair-setting lotion composition is prepared:

| | |
|---|---|
| Dye of Example 4 | 0.1 g |
| Vinyl acetate-crotonic acid copolymer (90% vinyl acetate, 10% crotonic acid, molecular weight 45,000 to 50,000) | 1 g |
| Ethyl alcohol, 96° titer | 25 g |
| Water, q.s.p. | 100 g |
| Ammonia at 22° Be, q.s.p. pH 8.5 | |

This hair-setting lotion when applied to bleached hair, imparts thereto a pearly pink shade.

EXAMPLE 55

The following hair-setting lotion composition is prepared:

| | |
|---|---|
| Dye of Example 10 | 0.5 g |
| Vinyl acetate-crotonic acid copolymer (90% vinyl acetate, 10% crotonic acid, molecular weight 45,000 to 50,000) | 2 g |
| Ethyl alcohol, 96° titer | 50 g |
| Water, q.s.p. | 100 g |
| Triethanolamine, q.s.p. pH 7.5 | |

This hair-setting lotion composition when applied to bleached hair, imparts thereto a very intense mauve shade.

EXAMPLE 56

The following hair-setting lotion composition is prepared:

| | |
|---|---|
| Dye of Example 13 | 0.08 g |
| Vinyl acetate-crotonic acid copolymer (90% vinyl acetate, 10% crotonic acid, average molecular weight 45,000 to 50,000) | 2 g |
| Ethyl alcohol, 96° titer | 50 g |
| Water, q.s.p. | 100 g |
| Ammonia at 22° Be, q.s.p. pH 6 | |

This hair-setting lotion when applied to bleached hair imparts thereto a pale pink shade with golden glints.

EXAMPLE 57

The following hair-setting lotion composition is prepared:

| | |
|---|---|
| Dye of Example 23 | 0.08 g |
| Vinyl acetate-crotonic acid copolymer (90% vinyl acetate, 10% crotonic acid, average molecular weight 45,000 to 50,000) | 2 g |
| Ethyl alcohol, 96° titer | 50 g |
| Water, q.s.p. | 100 g |
| Ammonia at 22° Be, q.s.p. pH 6 | |

This hair-setting lotion when applied to bleached hair imparts thereto a pale golden green shade.

EXAMPLE 58

The following hair-setting lotion composition is prepared:

| | |
|---|---|
| Dye of Example 2 | 0.11 g |
| Vinyl acetate-crotonic acid copolymer (90% vinyl acetate, 10% crotonic acid, molecular weight 45,000 to 50,000) | 2 g |
| Ethyl alcohol, 96° titer | 50 g |
| Water, q.s.p. | 100 g |
| Ammonia at 22° Be, q.s.p. pH 9 | |

This hair-setting lotion when applied to bleached hair imparts thereto a silvery beige gray shade.

EXAMPLE 59

The following hair-setting lotion composition is prepared:

| | |
|---|---|
| Dye of Example 5 | 0.1 g |
| Vinyl acetate-crotonic acid copolymer (90% vinyl acetate, 10% crotonic acid, molecular weight 45,000 to 50,000) | 2 g |
| Ethyl alcohol, 96° titer | 50 g |
| Water, q.s.p. | 100 g |
| Ammonia at 22° Be, q.s.p. pH 9 | |

This hair-setting lotion when applied to bleached hair imparts thereto a pearly pink blond shade.

EXAMPLE 60

The following hair-setting lotion composition is prepared:

| | |
|---|---|
| Dye of Example 21 | 0.05 g |
| Vinyl acetate-crotonic acid copolymer (90% vinyl acetate, 10% crotonic acid, molecular weight 45,000 to 50,000) | 2 g |
| Isopropyl alcohol, 96° titer | 50 g |
| Water, q.s.p. | 100 g |
| Ammonia at 22° Be, q.s.p. pH 7 | |

This hair-setting lotion when applied to bleached hair imparts thereto a light pearly turquoise blue shade.

EXAMPLE 61

The following hair-setting lotion composition is prepared:

| | |
|---|---|
| Dye of Example 15 | 0.055 g |
| Vinyl acetate-crotonic acid copolymer (90% vinyl acetate, 10% crotonic acid, molecular weight 45,000 to 50,000) | 1.5 g |
| Ethyl alcohol, 96° titer | 35 g |
| Water, q.s.p. | 100 g |
| Ammonia at 22° Be, q.s.p. pH 9 | |

This hair-setting lotion when applied to bleached hair imparts thereto a pearly rose mauve shade.

EXAMPLE 62

The following hair-setting lotion composition is prepared:

| | |
|---|---|
| Dye of Example 4 | 0.005 g |
| Vinyl acetate-crotonic acid copolymer (vinyl acetate 90%, crotonic acid 10%, molecular weight 45,000 to 50,000) | 2 g |
| Ethyl alcohol, 96° titer | 50 g |
| Water, q.s.p. | 100 g |
| Ammonia at 22° Be, q.s.p. pH 8.5 | |

This hair-setting lotion when applied to bleached hair imparts thereto a golden blond shade with pink glints.

EXAMPLE 63

The following hair dye composition is prepared:

| | |
|---|---|
| Dye of Example 20 | 0.15 g |
| Ethyl alcohol, 96° titer | 30 g |
| Water, q.s.p. | 100 g |
| Ammonia at 22° Be, q.s.p. pH 9 | |

This hair dye composition when applied for 20 minutes to bleached hair imparts thereto, after rinsing and shampooing, a light turquoise blue shade.

EXAMPLE 64

The followng hair-setting lotion composition is prepared:

| Dye of Example 14 | 0.045 g |
|---|---|
| Vinyl acetate-crotonic acid copolymer (90% vinyl acetate, 10% crotonic acid, molecular weight 45,000 to 50,000) | 2 g |
| Ethyl alcohol, 96° titer | 50 g |
| Water, q.s.p. | 100 g |
| Ammonia at 22° Be, q.s.p. pH 7 | |

This hair-setting lotion when applied to bleached hair imparts thereto a pale green shade.

EXAMPLE 65

The following hair dye composition is prepared:

| Dye of Example 18 | 0.105 g |
|---|---|
| Ethyl alcohol, 96° titer | 20 g |
| Water, q.s.p. | 100 g |
| Ammonia at 22° Be, q.s.p. pH 9 | |

This hair dye composition when applied for 20 minutes to 95% naturally white hair, imparts thereto, after rinsing and shampooing, a rose beige shade.

EXAMPLE 66

The following hair dye composition is prepared:

| Dye of Example 18 | 0.1 g |
|---|---|
| 2,6-diamino 4-N,N-diethylamino-2 phenol trihydrochloride | 0.03 g |
| Ethyl alcohol, 96° titer | 20 g |
| Water, q.s.p. | 100 g |
| Ammonia at 22° Be, q.s.p. pH 9 | |

This hair dye composition when applied for 20 minutes to 95% naturally white hair, imparts thereto, after rinsing and shampooing, a dark copper blond shade.

EXAMPLE 67

The following hair dye composition is prepared:

| Dye of Example 8 | 0.1 g |
|---|---|
| 2-amino 4-methoxy phenol hydrochloride | 0.02 g |
| 4,4'-dihydroxy 3,5-dimethyl diphenylamine | 0.06 g |
| Ethyl alcohol, 96° titer | 20 g |
| Water, q.s.p. | 100 g |
| Ammonia at 22° Be, q.s.p. pH 9 | |

This hair dye composition when applied for 20 minutes to 95% naturally white hair, imparts thereto, after rinsing and shampooing, a slightly mauve silvery gray shade.

EXAMPLE 68

The following hair dye composition is prepared:

| Dye of Example 2 | 0.12 g |
|---|---|
| Ethyl alcohol, 96° titer | 30 g |
| 20 volume hydrogen peroxide | 50 g |
| Water, q.s.p. | 100 g |
| Ammonia at 22° Be, q.s.p. pH 9 | |

This hair dye composition when applied for 20 minutes to 95% naturally white hair, imparts thereto, after rinsing and shampooing, a silvery blue gray shade.

EXAMPLE 69

The following hair dye composition is prepared:

| Dye of Example 25 | 0.055 g |
|---|---|
| Ethyl alcohol, 96° titer | 20 g |
| Water, q.s.p. | 100 g |
| Ammonia at 22° Be, q.s.p. pH 10 | |

This hair dye composition when applied for 20 minutes to 95% naturally white hair, imparts thereto, after rinsing and shampooing, a silvery glycine shade.

EXAMPLE 70

The following hair dye composition is prepared:

| Dye of Example 26 | 0.08 g |
|---|---|
| Ethyl alcohol, 96° titer | 30 g |
| Water, q.s.p. | 100 g |
| The pH of this composition is 8. | |

This hair dye composition when applied for 20 minutes to bleached hair, imparts thereto, after rinsing and shampooing, an intense cyclamen shade.

EXAMPLE 71

The following hair dye composition is prepared:

| Dye of Example 8 | 0.035 g |
|---|---|
| Nitroorthophenylenediamine | 0.08 |
| Ethyl alcohol, 96° titer | 20 g |
| Water, q.s.p. | 100 g |
| Ammonia at 22° Be, q.s.p. pH 9.5 | |

This hair dye composition when applied for 20 minutes to 95% naturally white hair, imparts thereto, after rinsing and shampooing, a very luminous bronze green shade.

EXAMPLE 72

The following hair dye composition is prepared:

| Dye of Example 10 | 0.025 g |
|---|---|
| N-[(2',4'-diamino 5'-methyl) phenyl] benzoquinoneimine | 0.075 g |
| Nitrometaphenylenediamine | 0.04 g |
| Ethyl alcohol, 96° titer | 20 g |
| Water, q.s.p. | 100 g |
| Ammonia at 22° Be, q.s.p. pH 9.5 | |

This hair dye composition when applied for 20 minutes to 95% naturally white hair, imparts thereto, after rinsing and shampooing, a chestnut shade with golden glints.

What is claimed is:

1. A diphenylamine of the formula

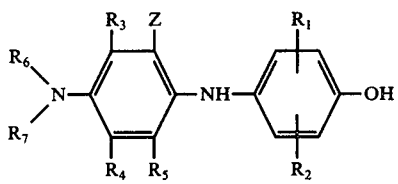

wherein $R_1$ is selected from the group consisting of methyl and chlorine, $R_2$ is selected from the group consisting of hydrogen and methyl, $R_3$ is selected from the group consisting of hydrogen and methyl, $R_4$ is selected from the group consisting of hydrogen, methyl and methoxy, $R_5$ is hydrogen, $R_6$ is selected from the group consisting of hydrogen and methyl, $R_7$ is selected from the group consisting of hydrogen and methyl, and Z is amino.

2. The diphenylamine of clam 1 in the form of an acid salt thereof.

3. The diphenylamine of claim 1 in the form of its hydrochloride salt.

* * * * *